United States Patent
Kase et al.

(10) Patent No.: US 11,966,669 B2
(45) Date of Patent: Apr. 23, 2024

(54) MOLTEN METAL COMPONENT ESTIMATION DEVICE, METHOD OF ESTIMATING MOLTEN METAL COMPONENT, AND METHOD OF MANUFACTURING MOLTEN METAL

(71) Applicant: JFE STEEL CORPORATION, Tokyo (JP)

(72) Inventors: Hiroto Kase, Tokyo (JP); Shinji Tomiyama, Tokyo (JP); Yukio Takahashi, Tokyo (JP); Shota Amano, Tokyo (JP); Toshifumi Kodama, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 759 days.

(21) Appl. No.: 17/054,968

(22) PCT Filed: Apr. 3, 2019

(86) PCT No.: PCT/JP2019/014829
§ 371 (c)(1),
(2) Date: Nov. 12, 2020

(87) PCT Pub. No.: WO2019/220800
PCT Pub. Date: Nov. 21, 2019

(65) Prior Publication Data
US 2021/0216680 A1    Jul. 15, 2021

(30) Foreign Application Priority Data
May 14, 2018   (JP) ................. 2018-092754

(51) Int. Cl.
*G06F 30/20*   (2020.01)
*C21C 5/30*   (2006.01)
*G01N 33/205*   (2019.01)

(52) U.S. Cl.
CPC ............... *G06F 30/20* (2020.01); *C21C 5/30* (2013.01); *G01N 33/205* (2019.01)

(58) Field of Classification Search
CPC .......... G06F 30/20; G01N 33/205; C21C 5/30
See application file for complete search history.

(56) References Cited

U.S. PATENT DOCUMENTS 5,984,998 A * 11/1999 Ottesen ................. G01N 21/39
75/375
2011/0045422 A1   2/2011 Tanca
2013/0018508 A1 * 1/2013 Reichel .................... C21C 5/30
700/274

FOREIGN PATENT DOCUMENTS

CN    101825567 A    9/2010
CN    102206727 A    10/2011
(Continued)

OTHER PUBLICATIONS

Li S, Wei X, Yu L. Numerical simulation of off-gas formation during top-blown oxygen converter steelmaking. Fuel. Apr. 1, 2011;90(4):1350-60. (Year: 2011) .*
(Continued)

*Primary Examiner* — Chuen-Meei Gan
(74) *Attorney, Agent, or Firm* — Oliff PLC

(57) ABSTRACT

A molten metal component estimation device including: an input device configured to receive measurement information about a refining facility including measurement results regarding an optical characteristic; a model database that stores model expressions and model parameters, regarding a blowing process reaction, including a model expression and model parameters representing a relation between the oxygen efficiency in decarburization and a carbon concentration in a molten metal in the refining facility; and a processor configured to: estimate component concentrations of the molten metal including the carbon concentration in the
(Continued)

molten metal by using the measurement information, the model expressions and the model parameters; estimate the carbon concentration in the molten metal based on the measurement results; and determine the model expression and the model parameters to be used when estimating the component concentrations of the molten metal, based on the estimation result of the carbon concentration in the molten metal.

3 Claims, 3 Drawing Sheets

(56) References Cited

FOREIGN PATENT DOCUMENTS

| | | | |
|---|---|---|---|
| CN | 102625891 A | 8/2012 | |
| CN | 104531936 A | 4/2015 | |
| CN | 205024254 U | 2/2016 | |
| CN | 106153550 A | 11/2016 | |
| JP | 62-67430 A | 3/1987 | |
| JP | S6318012 A | 1/1988 | |
| JP | H04308019 A | 10/1992 | |
| JP | 2000-146950 A | 5/2000 | |
| JP | 4677955 B2 | 4/2011 | |
| JP | 2017-008349 A | 1/2017 | |
| JP | 2017008349 A * | 1/2017 | ............... C21C 5/46 |
| JP | 2017089001 A | 5/2017 | |
| JP | 2017-115216 A | 6/2017 | |
| RU | 2180951 C1 | 3/2002 | |
| RU | 2539501 C2 | 1/2015 | |

OTHER PUBLICATIONS

Mar. 29, 2021 Office Action issued in Russian Patent Application No. 2020140778.

Nov. 26, 2021 Extended European Search Report issued in European Patent Application No. 19804356.4.

Oct. 8, 2021 Office Action issued in Chinese Patent Application No. 201980031713.5.

Jul. 2, 2019 International Search Report issued in International Patent Application No. PCT/JP2019/014829.

Feb. 17, 2022 Office Action issued in Korean Patent Application No. 10-2020-7034872.

* cited by examiner

MOLTEN METAL COMPONENT ESTIMATION DEVICE, METHOD OF ESTIMATING MOLTEN METAL COMPONENT, AND METHOD OF MANUFACTURING MOLTEN METAL

FIELD

The present invention relates to a molten metal component estimation device that estimates component concentrations of molten metal and slag in a refining facility of a steel industry, a method of estimating molten metal component, and a method of manufacturing a molten metal.

BACKGROUND

At ironworks, component concentrations and temperature of a hot metal tapped out of a blast furnace are adjusted in refining facilities, such as pretreatment facilities, converters, and secondary refining facilities. The converter process, among others, is a process of blowing oxygen into the converter to remove impurities from the molten metal and raise temperature thereof, and plays a very important role in terms of, for example, quality control of steel and rationalization of refining cost. In the converter process, to match the carbon concentration in the molten metal with a target carbon concentration in the molten metal at the time when the oxygen blowing is stopped, a model expression representing a relation between the oxygen efficiency in decarburization and the carbon concentration in the molten metal is generally used to control the oxygen feed amount or estimate the carbon concentration in the molten metal at the final stage of the blowing process. The oxygen efficiency in decarburization starts decreasing at the carbon concentration in the molten metal of around 0.4% (critical carbon concentration). Therefore, to obtain high calculation accuracy, it is important to perform the calculation of the model expression or switch the model expression at the time when the carbon concentration in the molten metal reaches the critical carbon concentration. Hereinafter, unless otherwise noted, the symbol % represents mass %, and various flow rates are represented in basic units of flow rate.

Patent Literature 1 describes a method of determining timing of sub-lance measurement taking into account a time required for dynamic control and a flow rate of the blown oxygen, in static control to determine the timing of the sub-lance measurement by using, for example, a model expression based on material input-output calculation before starting the blowing process, and in the dynamic control to determine the amount of the oxygen required to be blown until the carbon concentration in the molten metal reaches the target carbon concentration in the molten metal based on the carbon concentration in the molten metal obtained by the sub-lance measurement and using the model expression representing the relation between the carbon concentration in the molten metal and the oxygen efficiency in decarburization.

CITATION LIST

Patent Literature

Patent Literature 1: Japanese Patent No. 4677955
Patent Literature 2: Japanese Patent Application Laid-open No. 2017-115216

SUMMARY

Technical Problem

In the method described in Patent Literature 1, however, the timing of the sub-lance measurement is determined based on the static model. Therefore, according to the method described in Patent Literature 1, if an error is generated in the static model calculation by, for example, a measurement error in component concentrations of the molten metal or unknown disturbances during the blowing process, the sub-lance measurement may not be performed at the target carbon concentration in the molten metal, and a sufficient time may not be ensured for the dynamic control. If, in order to ensure the time for the dynamic control, the dynamic control is performed from a state where the carbon concentration in the molten metal is higher than the critical carbon concentration, the accuracy of the dynamic control may decrease because the oxygen efficiency in decarburization does not depend on the carbon concentration in the molten metal and is affected by decarburization due to iron oxide reduction in the slag, in the region where the carbon concentration in the molten metal is higher than the critical carbon concentration.

The present invention has been made in view of the above problems, and an object of the present invention is to provide a molten metal component estimation device and a method of estimating molten metal component capable of accurately estimating the carbon concentration in the molten metal, particularly at the final stage of the blowing process. It is another object of the present invention to provide a method of manufacturing a molten metal capable of manufacturing the molten metal having desired component concentrations at high yield.

Solution to Problem

To solve the problem and achieve the object, a molten metal component estimation device according to the present invention includes: an input device configured to receive measurement information about a refining facility including measurement results regarding an optical characteristic at a furnace throat in the refining facility during a blowing process; a model database configured to store model expressions and model parameters, regarding a blowing process reaction, including a model expression and model parameters representing a relation between the oxygen efficiency in decarburization and a carbon concentration in a molten metal in the refining facility; a model calculation unit configured to estimate component concentrations of the molten metal including the carbon concentration in the molten metal by using the measurement information, the model expressions and the model parameters; and a model determination unit configured to: estimate the carbon concentration in the molten metal based on the measurement results; and determine the model expression and the model parameters to be used by the model calculation unit, based on the estimation result.

Moreover, in the molten metal component estimation device according to the present invention, the measurement results include an intensity change rate of a spectrum resulting from an iron oxide reduction reaction in a slag.

Moreover, a method of estimating molten metal component according to the present invention includes: a model calculation step of estimating component concentrations of a molten metal including a carbon concentration in the molten metal by using: measurement information about a refining facility including measurement results regarding an optical characteristic at a furnace throat in the refining facility during a blowing process; and model expressions and model parameters regarding a blowing process reaction including a model expression and model parameters representing a relation between the oxygen efficiency in decarburization and a carbon concentration in the molten metal in the refining facility; and a model determination step of: estimating the carbon concentration in the molten metal based on the measurement results; and determining the model expression and the model parameters to be used at the model calculation step based on the estimation result.

Moreover, in the method of estimating molten metal component according to the present invention, the measurement results include an intensity change rate of a spectrum resulting from an iron oxide reduction reaction in a slag.

Moreover, a method of manufacturing a molten metal according to the present invention includes: a step of adjusting a component concentration of a molten metal within a desired range based on estimated component concentration of the molten metal that is estimated using the method of estimating molten metal component according to the present invention.

Advantageous Effects of Invention

A molten metal component estimation device and a method of estimating molten metal component according to the present invention are capable of accurately estimating the carbon concentration in the molten metal, particularly at the final stage of the blowing process. A method of manufacturing a molten metal according to the present invention is capable of manufacturing the molten metal having a desired component concentration at high yield.

DESCRIPTION OF EMBODIMENT

The following describes in detail a molten metal component estimation device and operations thereof as an embodiment of the present invention with reference to the drawings.

Configuration

First, a configuration of the molten metal component estimation device as an embodiment of the present invention will be described with reference to FIG. 1.

Figure 1:
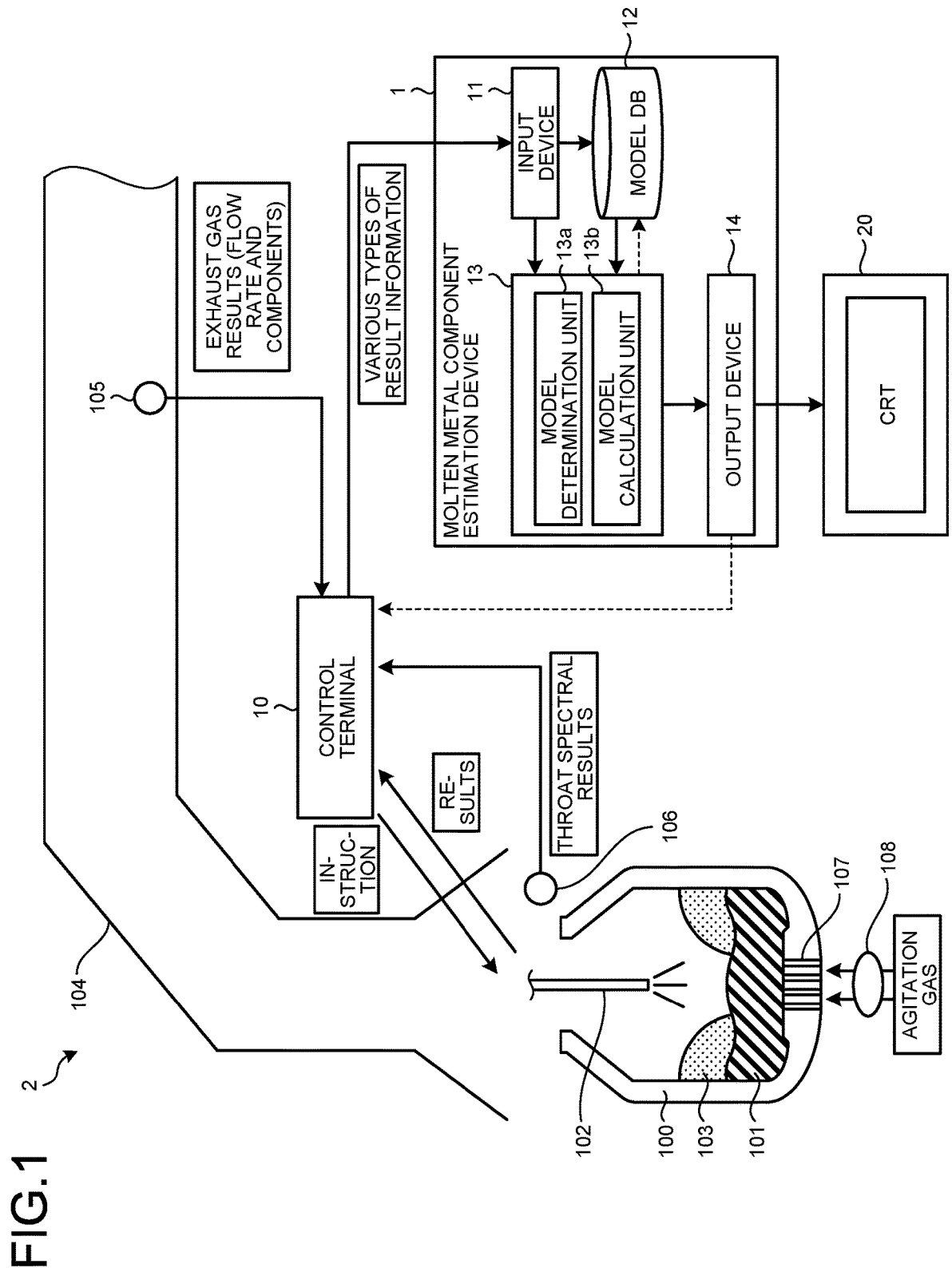
FIG. 1 is a schematic diagram illustrating a configuration of a molten metal component estimation device as an embodiment of the present invention.

FIG. 1 is a schematic diagram illustrating the configuration of the molten metal component estimation device as an embodiment of the present invention. As illustrated in FIG. 1, a molten metal component estimation device 1 as an embodiment of the present invention is a device that estimates component concentrations of a molten metal 101 and a slag 103 being processed in a refining facility 2 of a steel industry. The refining facility 2 includes a converter 100, a lance 102, and a duct 104. The lance 102 is disposed above the molten metal 101 in the converter 100. High-pressure oxygen (top-blown oxygen) is ejected from a distal end of the lance 102 toward the molten metal 101 below. Impurities in the molten metal 101 are oxidized by the high-pressure oxygen, and is taken into the slag 103 (blowing process). The duct 104 for guiding exhaust gas is provided above the converter 100.

An exhaust gas detector 105 is disposed in the duct 104. The exhaust gas detector 105 detects a flow rate of the exhaust gas discharged in association with the blowing process and components (for example, CO, $CO_2$, $O_2$, $N_2$, $H_2O$, and Ar) in the exhaust gas. The exhaust gas detector 105 measures the flow rate of the exhaust gas in the duct 104 based on, for example, differential pressure between before and after a Venturi tube provided in the duct 104. The exhaust gas detector 105 measures each of the component concentrations [%] of the exhaust gas. The flow rate and the component concentrations of the exhaust gas are measured, for example, at intervals of several seconds. Signals representing the detection results of the exhaust gas detector 105 are transmitted to a control terminal 10.

An agitation gas (bottom-blown gas) is blown into the molten metal 101 in the converter 100 through vent holes 107 formed at the bottom of the converter 100. The agitation gas is an inert gas, such as Ar. The blown-in agitation gas agitates the molten metal 101 to promote a reaction between the high-pressure oxygen and the molten metal 101. A flow meter 108 measures the flow rate of the agitation gas blown into the converter 100. The temperature and the component concentrations of the molten metal 101 are analyzed immediately before the blowing process starts and after the blowing process. The temperature and the component concentrations of the molten metal 101 are measured once or a plurality of times during the blowing process, and, for example, a supply amount (oxygen feed amount) and a rate (oxygen feed rate) of the high-pressure oxygen and the flow rate of the agitation gas (agitation gas flow rate) are determined based on the measured temperature and component concentration.

A blowing process control system to which the molten metal component estimation device 1 is applied includes the control terminal 10, the molten metal component estimation device 1, and a display device 20 as main components. The control terminal 10 is constituted by an information processing device, such as a personal computer or a workstation, and controls the oxygen feed amount, the oxygen feed rate, and the agitation gas flow rate so as to keep each of the component concentrations of the molten metal 101 within a desired range, and collects data of actual values of the oxygen feed amount, the oxygen feed rate, and the agitation gas flow rate.

The molten metal component estimation device 1 is constituted by an information processing device, such as a personal computer or a workstation. The molten metal component estimation device 1 includes an input device 11, a model database (model DB) 12, an arithmetic processor 13, and an output device 14.

The input device 11 is an input interface that receives various measurement results and result information regarding the refining facility 2. The input device 11 includes, for example, a keyboard, a mouse pointer, a pointing device, a data receiving device, and a graphical user interface (GUI). The input device 11 receives, for example, the result data and parameter setting values from the outside, and writes the received information to the model DB 12, and transmits it to the arithmetic processor 13. The input device 11 receives the measurement results regarding the temperature and the component concentrations of the molten metal 101 obtained at least either one of before the start and during the blowing process in the refining facility 2. The measurement results regarding the temperature and the component concentrations are supplied to the input device 11 through, for example, manual input by an operator or reading input from a recording medium. The input device 11 receives the result information from the control terminal 10. The result information includes, for example, the information on the flow rate and the component concentrations of the exhaust gas measured by the exhaust gas detector 105, information on an optical characteristic at a furnace throat of the converter 100 (furnace throat spectral results and furnace throat optical characteristic information) measured by a spectrometer 106, the information on the oxygen feed amount and the oxygen feed rate, the information on the agitation gas flow rate, information on charge amounts of raw materials (main raw material and auxiliary raw materials), and the temperature information on the molten metal 101.

The model DB 12 is a storage device that stores information on model expressions and parameters (model parameters) regarding a blowing process reaction in the refining facility 2. The model expressions include at least a decarburization model expression representing a relation between a carbon concentration in the molten metal 101 and the oxygen efficiency in decarburization during the blowing process. The oxygen efficiency in decarburization refers to an amount of carbon removed from the molten metal 101 relative to a unit amount of oxygen blown into the converter 100. The model DB 12 also stores various types of information received by the input device 11 and calculation/analysis results included in blowing process results calculated by the arithmetic processor 13.

The arithmetic processor 13 is an arithmetic processing device, such as a central processing unit (CPU), and controls overall operations of the molten metal component estimation device 1. The arithmetic processor 13 has functions as a model determination unit 13a and a model calculation unit 13b. For example, the arithmetic processor 13 executes computer programs to implement the model determination unit 13a and the model calculation unit 13b. The arithmetic processor 13 executes a computer program for the model determination unit 13a to serve as the model determination unit 13a, and executes a computer program for the model calculation unit 13b to serve as the model calculation unit 13b. The arithmetic processor 13 may include dedicated arithmetic devices or arithmetic circuits that serve as the model determination unit 13a and the model calculation unit 13b.

The molten metal component estimation device 1 having such a configuration executes a molten metal component estimation process described below to accurately estimate the component concentrations of the molten metal 101 and the slag 103, particularly at the final stage of the blowing process. The following describes, with reference to a flowchart illustrated in FIG. 2, the operations of the molten metal component estimation device 1 when performing the molten metal component estimation process.

Molten Metal Component Estimation Process

Figure 2:
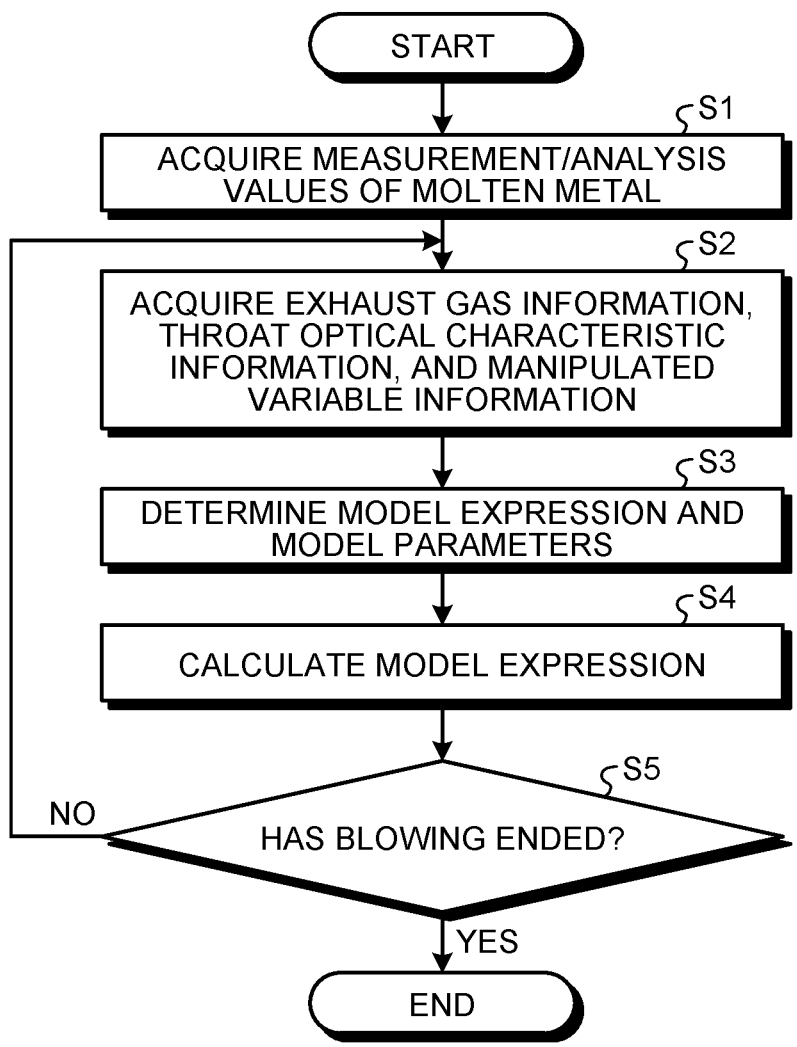
FIG. 2 is a flowchart illustrating a flow of a molten metal component estimation process as an embodiment of the present invention.

FIG. 2 is the flowchart illustrating the flow of the molten metal component estimation process as an embodiment of the present invention. The flowchart illustrated in FIG. 2 starts at the time when the blowing process has started, and the molten metal component estimation process proceeds to a process at Step S1.

In the process at Step S1, the arithmetic processor 13 acquires the measurement/analysis values of the molten metal 101. Specifically, the arithmetic processor 13 acquires the measurement/analysis results obtained by the temperature measurement and the component analysis on a sample of the molten metal 101. Thus, the process at Step S1 is completed, and the molten metal component estimation process proceeds to a process at Step S2.

In the process at Step S2, the arithmetic processor 13 acquires the exhaust gas measurement/analysis information (exhaust gas information), the furnace throat optical characteristic information, and manipulated variable information from the control terminal 10. In a normal converter blowing operation, the exhaust gas information, the furnace throat optical characteristic information, and the manipulated variable information are collected at regular intervals. If a large time-lag is present between the time of acquisition of the manipulated variable information and the time of acquisition of the exhaust gas information, the time-lag is taken into account (the exhaust gas information is accelerated by the time-lag) to create the data. If the measurement values and the analysis values include large amounts of noise, the measurement values and the analysis values may be replaced with values after being subjected to smoothing processing, such as moving average calculation. Moreover, errors included in the measurement value of the exhaust gas flow rate and the analysis values of CO and $CO_2$ are preferably corrected. Thus, the process at Step S2 is completed, and the molten metal component estimation process proceeds to a process at Step S3.

In the process at Step S3, the model determination unit 13a determines a model expression and model parameters to be used in the calculation by the model calculation unit 13b from among the model expressions and the model parameters stored in the model DB 12 based on the furnace throat optical characteristic information acquired in the process at Step S2. Specifically, a waveband of wavelength from 550 nm to 650 nm is selected from a waveband (spectrum) of light emitted in association with a decarburization reaction resulting from an iron oxide reduction reaction in the slag as represented by the following Reaction Equation (1), and the maximum value of the emission intensity in the selected waveband is detected as the optical characteristic at the furnace throat of the converter 100. It is known that when the carbon concentration in the molten metal reaches the vicinity of a critical carbon concentration, the efficiency of the decarburization reaction represented by the following Reaction Equation (1) decreases and the emission intensity also decreases.

$$FeO+C \rightarrow Fe+CO \quad (1)$$

Figure 3:
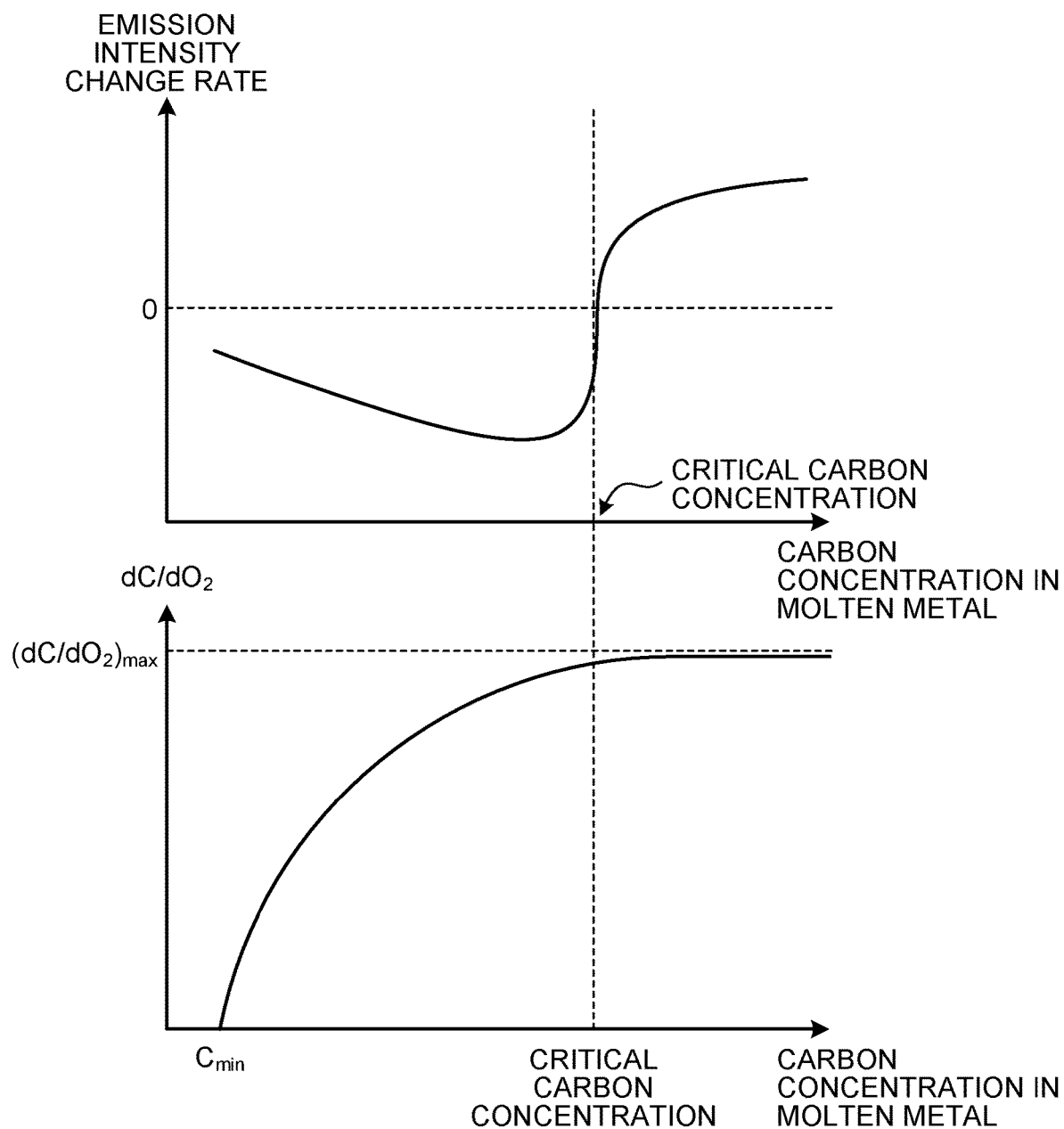
FIG. 3 depicts diagrams illustrating examples of a relation between a carbon concentration in a molten metal and an emission intensity change rate and a relation between the carbon concentration in the molten metal and the oxygen efficiency in decarburization.

Accordingly, as illustrated in FIG. 3(a), the model determination unit 13a calculates a change rate of the maximum value of the emission intensity (emission intensity change rate), and detects a time when the emission intensity change rate shifts from a positive value to a negative value as a time when the carbon concentration in the molten metal reaches the critical carbon concentration. In a region where the carbon concentration in the molten metal is higher than the critical carbon concentration, the model determination unit 13a selects a mass input-output calculation expression based on the exhaust gas information and the manipulated variable information or a model expression, such as a physical reaction model calculation expression, and model parameters from the model DB 12. After the time when the carbon concentration in the molten metal reaches the critical carbon concentration, the carbon concentration in the molten metal enters a region where the oxygen efficiency in decarburization depends on the carbon concentration in the molten metal as illustrated in FIG. 3(*b*). Accordingly, the model determination unit 13*a* selects the decarburization model expression and model parameters thereof from the model DB 12. In the present invention, the form of the model expression selected from the model DB 12 does not matter. The method of switching the model expression may be, for example, a method of changing the model parameters so as to change the degree of contribution of the decarburization model expression to the model calculation. Thus, the process at Step S3 is completed, and the molten metal component estimation process proceeds to a process at Step S4.

In the process at Step S4, the model calculation unit 13*b* uses the model expression and the model parameters determined (selected) in the process at Step S3 to calculate the component concentrations of the molten metal 101 including the carbon concentration in the molten metal, and outputs the information on the calculated component concentrations of the molten metal 101 to the output device 14. For example, Patent Literature 2 describes details of a method of calculating the component concentrations of the molten metal 101. Thus, the process at Step S4 is completed, and the molten metal component estimation process proceeds to a process at Step S5.

In the process at Step S5, the arithmetic processor 13 determines whether the blowing process has been completed. If the result of the determination indicates that the blowing process has been completed (Yes at Step S5), the arithmetic processor 13 ends the series of molten metal component estimation process. If, instead, the blowing process has not ended (No at Step S5), the arithmetic processor 13 returns the molten metal component estimation process to the process at Step S2.

As is clear from the above description, in the molten metal component estimation process as an embodiment of the present invention, the model determination unit 13*a* estimates the carbon concentrations of the molten metal 101 based on the furnace throat optical characteristic information, and based on the estimation results, determines the model expression and the model parameters to be used by the model calculation unit 13*b*. More in detail, the model determination unit 13*a* detects the time when the carbon concentration of the molten metal 101 has reached the critical carbon concentration based on the furnace throat optical characteristic information, and switches the model expression and the model parameters used by the model calculation unit 13*b* to the model expression and the model parameters based on the relation between the carbon concentration of the molten metal and the oxygen efficiency in decarburization at the time when the carbon concentration in the molten metal 101 has reached the critical carbon concentration. Through this process, the carbon concentration of the molten metal 101 can be accurately estimated, particularly at the final stage of the blowing process.

While the embodiment to which the invention made by the present inventors is applied has been described, the present invention is not limited to the description and the drawings constituting a part of the disclosure of the present invention by way of the present embodiment. The model switching in the estimation calculation of the carbon concentration in the molten metal has been described in the present embodiment. However, for example, when the control is performed using a static model and a dynamic model as described in the method of Patent Literature 1, dynamic model control can be performed at appropriate timing by acquiring the dynamic model from the model DB 12 based on the furnace throat optical characteristic measurement information. Thus, other embodiments, examples, operational techniques, and the like made by those skilled in the art based on the present embodiment are all included in the scope of the present invention.

INDUSTRIAL APPLICABILITY

The present invention can provide a molten metal component estimation device and a method of estimating molten metal component capable of accurately estimating the carbon concentration in the molten metal, particularly at the final stage of the blowing process.

REFERENCE SIGNS LIST

1 Molten metal component estimation device
2 Refining facility
10 Control terminal
11 Input device
12 Model database (model DB)
13 Arithmetic processor
13*a* Model determination unit
13*b* Model calculation unit
14 Output device
20 Display device
100 Converter
101 Molten metal
102 Lance
103 Slag
104 Duct
105 Exhaust gas detector
106 Spectrometer
107 Vent holes
108 Flow meter

The invention claimed is:

1. A molten metal component estimation device comprising:
an input device configured to receive measurement information about a refining facility including measurement results regarding an optical characteristic at a furnace throat in the refining facility during a blowing process;
a model database configured to store model expressions and model parameters, regarding a blowing process reaction, including a model expression and model parameters representing a relation between the oxygen efficiency in decarburization and a carbon concentration in a molten metal in the refining facility; and
a processor comprising hardware, the processor being configured to:
estimate component concentrations of the molten metal including the carbon concentration in the molten metal by using the measurement information, the model expressions and the model parameters,
estimate the carbon concentration in the molten metal based on the measurement results,
determine the model expression and the model parameters to be used when estimating the component concentrations of the molten metal, based on the estimation result of the carbon concentration in the molten metal, and
detect a time when the intensity change rate shifts from a positive value to a negative value as a time when the carbon concentration in the molten metal reaches a critical carbon concentration, and switch the model expression and the model parameters based on the critical carbon concentration, wherein the measurement results include an intensity change rate of a spectrum resulting from an iron oxide reduction reaction in a slag, and the molten metal component estimation device is configured to adjust the component concentration of the molten metal within a desired range at the blowing process based on the estimated component concentration of the molten metal that is estimated to form an adjusted molten metal.

2. A method of estimating molten metal component, comprising:

estimating component concentrations of a molten metal including a carbon concentration in the molten metal by using:

measurement information about a refining facility including measurement results regarding an optical characteristic at a furnace throat in the refining facility during a blowing process, and model expressions and model parameters regarding a blowing process reaction including a model expression and model parameters representing a relation between the oxygen efficiency in decarburization and a carbon concentration in the molten metal in the refining facility;

estimating the carbon concentration in the molten metal based on the measurement results;

determining the model expression and the model parameters to be used when estimating the component concentrations of the molten metal based on the estimation result of the carbon concentration in the molten metal;

detecting a time when the intensity change rate shifts from a positive value to a negative value as a time when the carbon concentration in the molten metal reaches a critical carbon concentration, and switching the model expression and the model parameters based on the critical carbon concentration; and adjusting the component concentration of the molten metal within a desired range at the blowing process based on the estimated component concentration of the molten metal that is estimated to form an adjusted molten metal, wherein the measurement results include an intensity change rate of a spectrum resulting from an iron oxide reduction reaction in a slag.

3. A method of manufacturing a molten metal, comprising adjusting a component concentration of a molten metal within a desired range based on estimated component concentration of the molten metal that is estimated using the method of estimating molten metal component according to claim 2.

* * * * *